(12) United States Patent
Ramaiah et al.

(10) Patent No.: US 7,998,935 B2
(45) Date of Patent: Aug. 16, 2011

(54) QUINALDINE BASED SEMISQUARAINES AND SQUARAINE DYES, PROCESS FOR PREPARATION THEREOF AND USE THEREOF

(75) Inventors: Danaboyina Ramaiah, Kerala (IN); Jyothish Kuthanapillil, Kerala (IN); Kalliat Thazhathveetil Arun, Kerala (IN)

(73) Assignee: Council of Scientific and Industrial Research, New Delhi (IN)

( * ) Notice: Subject to any disclaimer, the term of this patent is extended or adjusted under 35 U.S.C. 154(b) by 1256 days.

(21) Appl. No.: 11/650,567

(22) Filed: Jan. 8, 2007

(65) Prior Publication Data
US 2007/0167350 A1    Jul. 19, 2007

(30) Foreign Application Priority Data
Jan. 6, 2006 (IN) .................. 60/DEL/2006

(51) Int. Cl.
| A61K 31/70 | (2006.01) |
| A61K 31/4052 | (2006.01) |
| A61K 31/7042 | (2006.01) |
| A61K 31/7028 | (2006.01) |

(52) U.S. Cl. ............ 514/25; 514/23; 514/176; 514/311; 514/1.1; 536/17.4; 536/4.1; 540/107; 546/176; 530/300

(58) Field of Classification Search .............. 514/23, 514/2, 176, 311, 25, 1.1; 536/17.4, 4.1; 540/107; 546/176; 530/300
See application file for complete search history.

(56) References Cited

U.S. PATENT DOCUMENTS
3,592,657 A * 7/1971 Kampfer ............... 430/594

OTHER PUBLICATIONS

Jyothish et al. (Organic Letters (2004), vol. 6, No. 22, 3965-3968).*
Jyothish et al., Organic Letters—supporting Information, vol. 6, No. 22, 2004, pp. S1-S13.*
PCT Notification dated Jan. 17, 2008.
International Search Report dated Jan. 17, 2008 in PCT/IB2007/000030.
Written Opinion dated Jan. 17, 2008 in PCT/IB2007/000030.
Jyothish, K. et al, Organic Letters, vol. 6, No. 22, 2004 pp. 3965-3968 "Synthesis of novel Quinaldine-Based Squaraine Dyes: Effect of Substituents and Role of Electronic Factors."
Jyothish, K. et al, Organic Letters—supporting Information, vol. 6, No. 22, 2004, pp. S1-S13, "Synthesis of novel Quinaldine-Based Squaraine Dyes: Effect of Substituents and Role of Electronic Factors."
S. Yagi et al, Synthesis, No. 3, 2002, pp. 413-417, "Synthesis of Near-Infrared absorbing Disquarylium Dyues bearing unsymmetrically extended pi-Conjugation Structures."
A. Hirth, et al, Chemie in Unserer Zeit, vol. 33, No. 2, 1999, pp. 83-94, "Photodynamische Tumortherapie."

* cited by examiner

*Primary Examiner* — Shaojia Anna Jiang
*Assistant Examiner* — Michael C Henry
(74) *Attorney, Agent, or Firm* — Nixon & Vanderhye P.C.

(57) ABSTRACT

The present invention provides quinaldine-based semisquaraines, symmetrical and unsymmetrical squaraine dyes represented by the general formulae 1, 2 and 3 and/or pharmaceutically acceptable derivatives thereof as sensitizers for photodynamic therapeutical and industrial applications. These symmetrical and unsymmetrical squaraine dyes posses absorption which extends well into the photodynamic window (650-800 nm) and hence are useful for the treatment of deep seated tumors. The absorption of these dyes can be tuned by changing the substituents on the quinaldine moiety thereby enabling the development of a library of dyes which have absorption ranging from 650 to 800 nm. They also exhibited fluorescence emission in the long wavelength region making them useful as near infrared fluorescence sensors for the detection of tumors. These dyes are non-toxic in the dark and exhibit good photocytotoxicity. Accordingly the quinaldine based semisquaraines, symmetrical and unsymmetrical squaraines are extremely useful as diagnostic and therapeutic agents for photodynamic therapeutical and industrial applications.

20 Claims, 3 Drawing Sheets

Figure 1:
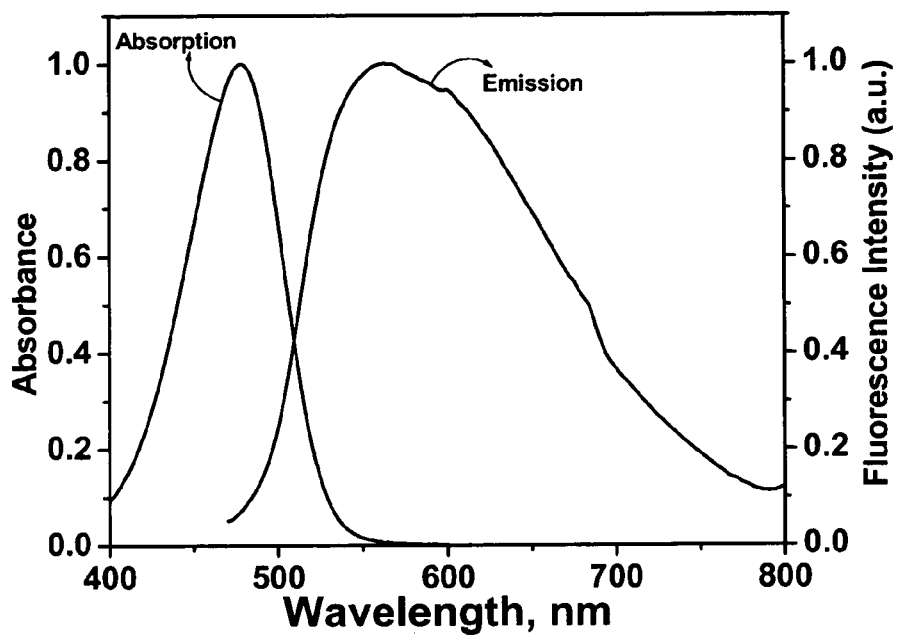

QUINALDINE BASED SEMISQUARAINES AND SQUARAINE DYES, PROCESS FOR PREPARATION THEREOF AND USE THEREOF

This application is a new U.S. utility application claiming benefit of IN 60/DEL/2006, dated 6 Jan. 2006, the entire content of which is hereby incorporated by reference.

The present invention relates to quinaldine based semisquaraines of the general formula 1 and squaraine dyes of the general formulae 2 and 3, respectively as shown below

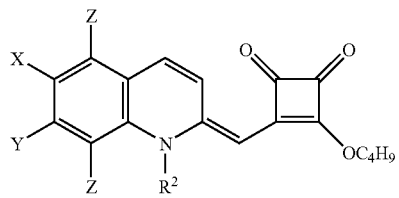

Formula 1 wherein, X=H, I, Br, $NO_2$, CN, COOH, $SO_3H$ or $OR^1$, wherein $R^1$=H, alkyl groups having from 1 to 6 carbon atoms, glycols having from 2 to 4 ethylene groups, cholic acid, cholesterol, sugar, amino acids or peptides, wherein Y=H, I, or Br, wherein, Z=H, I, Br, $NO_2$, CN, COOH, $SO_3H$, $SO_2Cl$ or $OR^1$, wherein R=alkyl groups having from 1 to 6 carbon atoms, glycols having from 2 to 4 ethylene groups, alkyl sulphonic acids and acid chlorides having from 1 to 6 carbon atoms

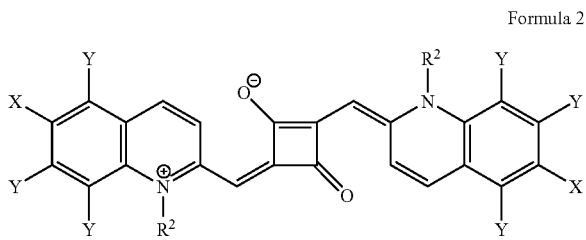

Formula 2 wherein, X=H, I, Br, $NO_2$, CN, COOH, $SO_3H$, $SO_2Cl$ or $OR^1$, wherein, $R^1$=H, alkyl groups having from 1 to 6 carbon atoms, glycols having from 2 to 4 ethylene groups, cholic acid, cholesterol, sugar, amino acids or peptides, wherein, Y=H, I, Br, $NO_2$, CN, COOH, $SO_3H$, $SO_2Cl$ or $OR^1$, wherein $R^2$=alkyl groups having from 1 to 6 carbon atoms, glycols having from 2 to 4 ethylene groups, alkyl sulphonic acids and acid chlorides having from 1 to 6 carbon atoms

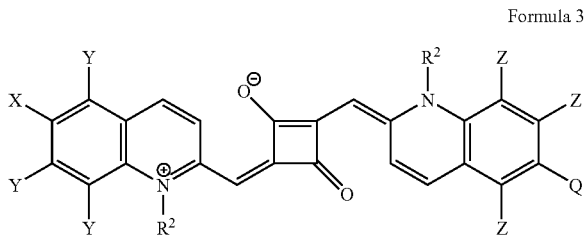

Formula 3 wherein, X=$OR^1$, wherein, $R^1$=H, alkyl groups having from 1 to 6 carbon atoms, glycols having from 2 to 4 ethylene groups, cholic acid, cholesterol, sugar, amino acids or peptides, wherein Y=H, I, Br, $NO_2$, CN, COOH, $SO_3H$, $SO_2Cl$ or $OR^1$, wherein Q=H, I, Br, $NO_2$, CN, COOH, $SO_3H$, $SO_2Cl$, wherein Z=H, I, Br, $NO_2$, CN, COOH, $SO_3H$, $SO_2Cl$, wherein $R^2$=alkyl groups having from 1 to 6 carbon atoms, glycols having from 2 to 4 ethylene groups, alkyl sulphonic acids and acid chlorides having from 1 to 6 carbon atoms; and pharmaceutically acceptable derivatives thereof for photodynamic therapeutical, diagnostic and industrial applications.

The present invention also relates to a process for the preparation of quinaldine based semisquaraines of the general formula 1 and squaraine dyes of the general formulae 2 and 3 and use of such sensitizers for photodynamic, therapeutical, diagnostic and industrial applications.

The present invention also relates to semisquaraines and squaraine dyes of the general formulae 1, 2 and 3 or pharmaceutically acceptable derivatives thereof, for use as photosensitizers in photodynamic applications for the detection and treatment of cancer and other diseases in human beings or animals.

The present invention also relates to semisquaraines and squaraine dyes of the general formulae 1, 2 and 3 or pharmaceutically acceptable derivatives thereof for use as near-infrared fluorescence probes for biological applications.

The present investigation also relates to quinaldine based semisquaraines of the general formula 1, which can be used as potential protein tyrosine phosphatases (PTPases) inhibitors and squaraine dyes of the general formulae 2 and 3 for use in the detection of metal ions in the biological media.

The present invention also relates to a process for the preparation of quinaldine based semisquaraines of the general formula 1 and squaraine dyes of the general formulae 2 and 3 and/or their derivatives for photodynamic industrial applications such as sterilization of fluids and water and related other applications.

Photodynamic therapy is an emerging modality for the diagnosis and treatment of cancer and various diseases. The large body of evidence suggests that photodynamic therapy represents a convenient and effective approach for a variety of cancers. The process requires the presence of a photosensitizing agent, which is capable of being taken up by target cells and tissues and which, on irradiation by light of a particular wavelength, generates species which are toxic to those cells and tissues. Photodynamic therapy has advantages over many other conventional therapies due to the selectivity of the photodynamic process. There is more sensitizer in tumor tissues than in the normal tissues. This reduces the potential for destruction of normal tissues. In addition the ability to direct light specifically onto the target cells and tissues by the use of fiber-optic technology further increased the selectivity of this process. Furthermore, the use of photosensitizing agents, which produce no response until irradiated with light, reduces significantly the potential for side effects, which may complicate the process.

The only sensitizer that has been extensively studied is a hematoporphyrin derivative (HpD), also known as first generation photosensitizer. HpD and its commercial variants Photofrin (porfine sodium), Photosan, Photogen were the first ones to be approved in clinical use and for which first regulatory authorizations were obtained. However, Photofrin is at the disadvantage of being a mixture of products the composition of which is highly sensitive to the synthetic methodology adopted. It is known to cause cutaneous photosensitivity as an undesirable side effect because of its slow release from the body. Under these circumstances, a patient treated with Photofrin is required to stay in the dark for a long period until it is excreted from the body. Photofrin possesses only weak absorption in the red region of spectrum (the molar absorption coefficient being as small as 3000 M$^{-1}$ cm$^{-1}$ at 630 nm), leading to difficulty in delivering light to some tumor sites and also incomplete light penetration of larger tumors. Therefore, photodynamic therapy using Photofrin is only indicated for cancers developing in the surface layers of less than 10 mm depth. References may be made to Dougherty, T. J. *Photochem. Photobiol.* 1987, 45, 879; Kessel, D.; Dougherty, T. J. Phorphyrin Photosensitization; Plenum Publishing Corp. New York, 1983; Brown, S. B.; Truscott, T. G. *Chem. Ber,* 1993, 29, 955; Andreoni, A., Cubeddu, R. Phorphyrins in Tumor Phototherapy; Plenum Publishing Corp.: New York, 1984; Brasseur, N.; Hasarat, A., Langlois, R., Wagner, J. R; Rousseau, J.; van Lier J. E. *Photochem. Photobiol.* 1987, 45, 581; Spikes, J. D, *Photochem. Photobiol.* 1986, 43, 691; Firey, P. A.; Ford, W. E.; Sounik, J. R.; Kenney, M. E.; Rodgers, M. A. J. *J. Am. Chem. Soc.* 1988, 110, 7626; Moan, J. *Cancer Lett.* 1986, 33, 45; Tralau, C J., Young, A. R.; Walker, N. P. J.; Vernon, D. I.; MacRobert, A. J., Brown, S. B.; Brown, S. G. *Photochem. Photobiol.* 1989, 49, 305. Bonnett, R. *Chem. Soc. Rev.* 1995, 24, 19; Lane, N. *Scientific American* 2003, 38-45.

To overcome the drawbacks of the first generation sensitizers, second generation photosensitizers that exhibit strong absorption in the long wavelength region have been synthesized. Second generation sensitizers that are under evaluation at various clinical phases of photodynamic therapy include chlorins, porphycenes, benzoporphyrins, phthalocyanins, purpurins and aminolevulinic acid-mediated porphyrins. Purpurins possess favorable optical properties and biodistribution patterns but require solubilizing or emulsifying agents such as liposomes or lipoproteins for their photodynamic applications. Chlorins have strong absorption in the red and infrared regions of the spectrum and compete favorably with Photofrin, but skin photosensitivity is a major problem with them. Phthalocyanins and metallophthalocyanins have been found to have strong absorption in the 600-700 nm regions, but details of the extent of sulfonation versus the photodynamic activity is not clear. References may be made to U.S. Pat. Nos. 603,267; 5,965,598; 5,889,181; 586,035; 5,789, 586; Kostenich, G. A.; Zuravkin, I. N.; Zhavrid, E. A. *J Photochem. Photobiol. B. Biol.* 1994, 22, 211; Leach, M. W.; Higgins, R. J.; Autry, S. A.; Boggan, J. E.; Lee, S.-J. H.; Smith, K. M. *Photochem. Photobiol.* 1993, 1616, 275; Vogel, E.; Kocher, M Schmickler, H.; Lex, J. *Angew. Chem. Int. Ed. Engl.* 1986, 25, 197; Leunig, M.; Richert, C.; Gamarra, F.; Lumper, W.; Vogel, E.; Jochani D.; Goetz, A. E. *Br. J. Cancer* 1993, 68, 225; Boyle, R. W.; Legnoff, C. C.; Vanheir, J. E. *Br. J. Cancer,* 1993, 67, 1177; Wohrl, D.; Shopova, M.; Muller, S.; Muleiv, A. D.; Mantereva, V. N.; Krastev, K. K. *J Photochem. Photobiol. B. Biol.* 1993, 21, 155; Morgan, A. R.; Garbo, G. M.; Keck, R. W.; Ericksen, L. D.; Selman, S. H. *Photochem. Photobiol.* 1990, 51, 589.

Development of photosensitizers, which have strong absorptions in the long wavelength region, non-toxic to normal tissues, soluble in buffer at physiological pH, can be bleached during the photodynamic treatment and exhibit higher therapeutic efficacy are still desired. Also the design of functional molecules that can target specific cancer cells are extremely important because of the biochemical and biomedical applications.

Squaraines form a class of dyes possessing sharp and intense absorption bands in the red to near infra red region. The photophysical and photochemical properties of these have been studied extensively, because their absorption and photochemical characteristics make them highly suitable for a number of industrial applications. These include photoreceptors in copiers, photoconductors in organic solar cells and IR absorbers in organic optical disks. Squaraines find industrial applications in xerographic photoreceptors, solar cells and optical recording devices. However, due to the very low intersystem crossing efficiency of these dyes, their potential as photosensitizers in photodynamic therapeutical applications has not yet been explored. References may be made to U.S. Pat. Nos. 6,001,523; 5,552,253; 5,444,463; Law, K.-Y. *Chem. Rev.* 1993, 93, 449; Piechowski, A P; Bird, G. R.; Morel, D L.; Stogryn, E. L. *J. Phy. Chem.* 1984, 88, 934. Accordingly, the use of squaraine based dyes was studied to observe if problems associated with the prior art could be overcome. Preliminary investigations indicated that halogenation of the squaraine moiety resulted in increased water solubility and intersystem crossing efficiency when compared to the parent unsubstituted squaraine dyes. These halogenated dyes exhibited strong absorption in the near infrared region (>600 nm) and significant bathochromic shifts in presence of microheterogeneous media. Triplet excited states were the main transients involved in these systems, which interact efficiently with molecular oxygen generating biologically highly reactive singlet oxygen in quantitative yields thereby making them potential candidates in photodynamic therapeutical applications. We have also investigated the cytotoxicity and mutagenicity of these dyes in the dark and under irradiation conditions. The results demonstrate that the halogenated squaraine dyes exhibit efficient cytotoxicity upon photoexcitation in two different types of mammalian cell lines (AS52 Chinese hamster ovary cells and L5178Y mouse limphoma cells). The cytotoxicities of the compounds under dark are much lower. Mechanistically, the cellular damage may be mediated by singlet oxygen, generated from photoexcited squaraine dyes. The squaraine dyes are also found to be only weekly mutagenic in the presence and absence of light. References may be made to Ramaiah, D.; Arun, K. T.; Das, S. and Epe, B. U.S. Pat. No. 6,770,787B2 (2004), Ramaiah, D.; Arun, K. T.; Das, S. and Epe, B. Indian patent No. 193540 (2004). Ramaiah, D.; Joy, A.; Chandrasekhar, N; Eldho, N. V.; Das, S.; George, M. V. *Photochem. Photobiol.* 1997, 65, 783; Arun, K. T.; Ramaiah, D.; Epe, B. *J. Phys. Chem. B* 2002, 107, 11622, Ramaiah, D.; Eckert, I; Arun, K. T.; Weidenfeller, L.; Epe, B. *Photochem. Photobiol.* 2002, 76, 672; Ramaiah, D.; Eckert, I; Arun, K. T.; Weidenfeller, L.; Epe, B. *Photochem. Photobiol.* 2004, 79, 99.

However, the absorption of these dyes is in the lower part of the photodynamic window, ~600 nm where most of the biological tissues absorb light. Hence the use of these compounds for the destruction of deep-seated tumors becomes difficult. In this context the present invention aims at the development of efficient sensitizers based on squaraine dyes which can be used for tumors located deep inside the body. Quinaldine based squaraine dyes are known to have absorption well beyond 700 nm, which suits well for applications in photodynamic therapy. References may be made to Santos, P. F.; Reis, L. V.; Almeida, P.; Oliveira, A. S.; Ferreira, L. F. V. *J. Photochem. Photobiol. A: Chem.* 2003, 160, 159.

The present invention is an attempt to develop squaraine-based dyes having absorption in the near infrared region, which can be used for the destruction as well as detection of deep-seated tumors. We have substituted the quinaldine based squaraine dyes with heavy atoms like bromine and iodine which enhance their intersystem crossing efficiency and thereby increase their ability to generate cytotoxic agents like singlet oxygen. We have also introduced various substituents on the benzo ring of the quinaldine moiety, which enables their physiological uptake. Moreover, we have developed conjugates of dye and cellular recognition elements like sugar, proteins, cholic acid and cholesterol, which enables site specific destruction of tumors. References may be made to Monsigny, M.; Roche, A. C.; Midoux, P.; Kieda, C.; Mayer, R. In *Lectins and Glycoconjugates in Oncology: Structure, Function, Clinical Application*; Gabius, H. J.; Nagel, G. A. Eds.; Springer: Heidelberg, 1988, p 1.

In the present invention we have synthesized novel quinaldine based squaraine dyes and investigated their photophysical properties under different conditions and photobiological properties in mammalian cell lines like mouse lymphoma L1210 cells.

The main object of the present invention is to provide efficient squaraine based dyes and/or pharmaceutical acceptable derivatives thereof, for use as sensitizers in photodynamic therapeutical applications including the treatment of cancer.

Another object of the invention is to provide efficient squaraine based dyes and/or pharmaceutical acceptable derivatives thereof, for use as sensitizers in photodynamic therapeutical applications for the detection of tumors.

Another object of the invention is to provide efficient squaraine based dyes and/or pharmaceutical acceptable derivatives thereof, for use as near-infrared fluorescence sensors for biological applications.

Still another object of the invention is to provide cellular recognition elements linked squaraine dyes like sugar, cholesterol and amino acids linked squaraine dyes and acceptable derivatives thereof in improving their efficiency as sensitizers for photodynamic applications.

Yet another object of the invention is to provide an efficient method for the synthesis of quinaldine based unsymmetrical squaraine dyes and derivatives thereof.

Yet another object of the invention is to provide an efficient method for the synthesis of quinaldine-based semisquaraines and derivatives thereof.

Yet another object of the invention is to provide quinaldine based semisquaraines, which can be used as potential protein tyrosine phosphatases (PTPases) inhibitors.

Another object of the invention is to provide squaraine based dyes and/or their derivatives for use as photodynamic industrial applications such as sterilization of fluids, water and related other applications.

Yet another object of the invention is to provide quinaldine based symmetrical and unsymmetrical squaraine dyes and semisquaraines and/or their derivatives thereof that can be used for the detection of biologically important metal ions under physiological condition.

In the drawings accompanying the specifications:

FIG. 1: Absorption and fluorescence emission spectra of semisquaraine of general formula 1, where X=OH, Y=H, Z=H, $R^2$=$CH_3$, in methanol FIG. 2: Absorption and fluorescence emission spectra of squaraine dyes of general formula 2, where X=I, Y=H, $R^2$=$CH_3$, in dimethyl sulfoxide.

Figure 3:
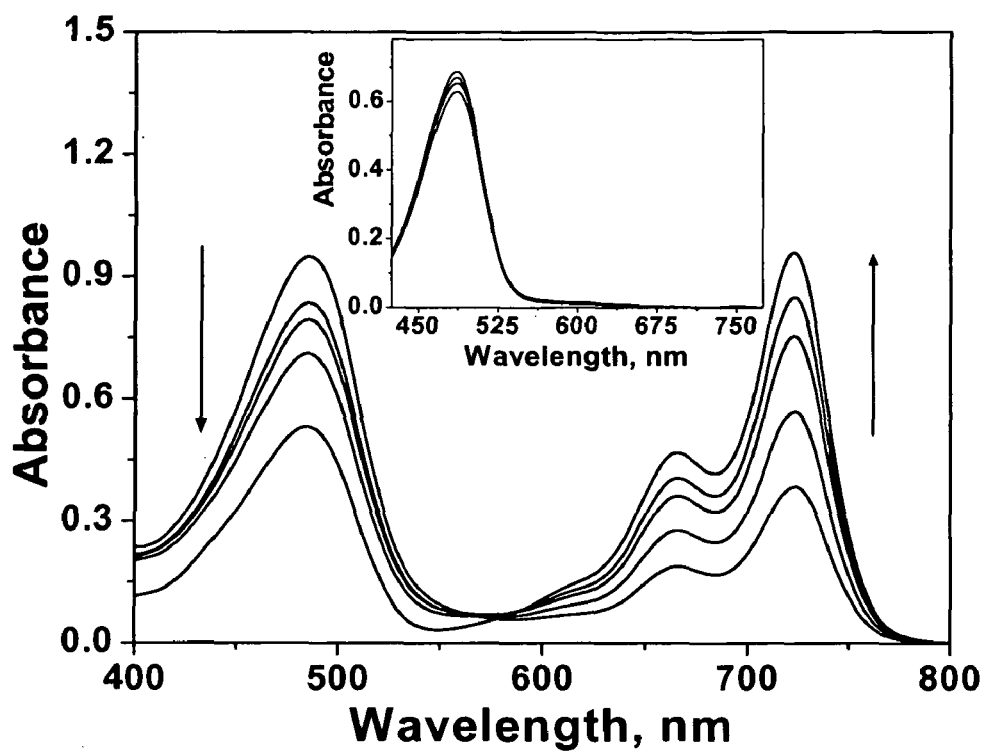

FIG. 3: Change in absorption spectra obtained for the reaction between the semisquaraine of the general formula 1, where X=OH, Y=H, Z=H, $R^2$=$CH_3$ and the 6-iodoquinaldinium salt at various time intervals. Inset shows the change in absorption spectra obtained for the reaction between the semisquaraine of the general formula 1, where X=OH, Y=H, Z=H, $R^2$=$CH_3$ and the 6-hydroxyquinaldinium salt at various time intervals.

Figure 4:
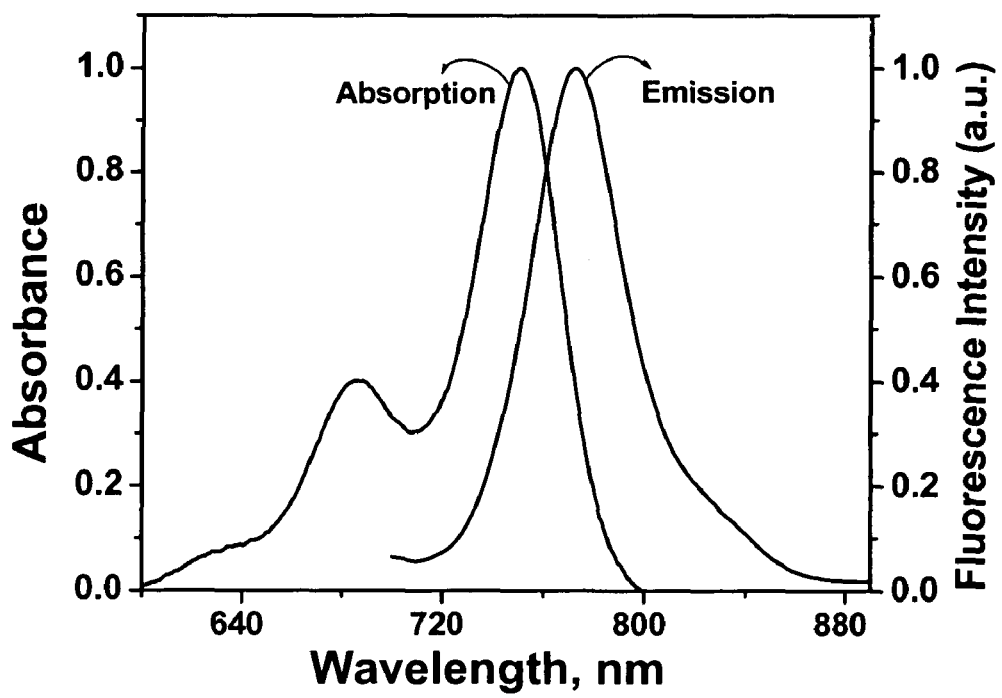

FIG. 4: Absorption and fluorescence emission spectra of unsymmetrical squaraine dyes of general formula 3, where X=$C_6H_{11}O_6$, Y=H, Q=I, Z=H, $R^2$=$CH_3$, in dimethyl sulfoxide.

Figure 5:
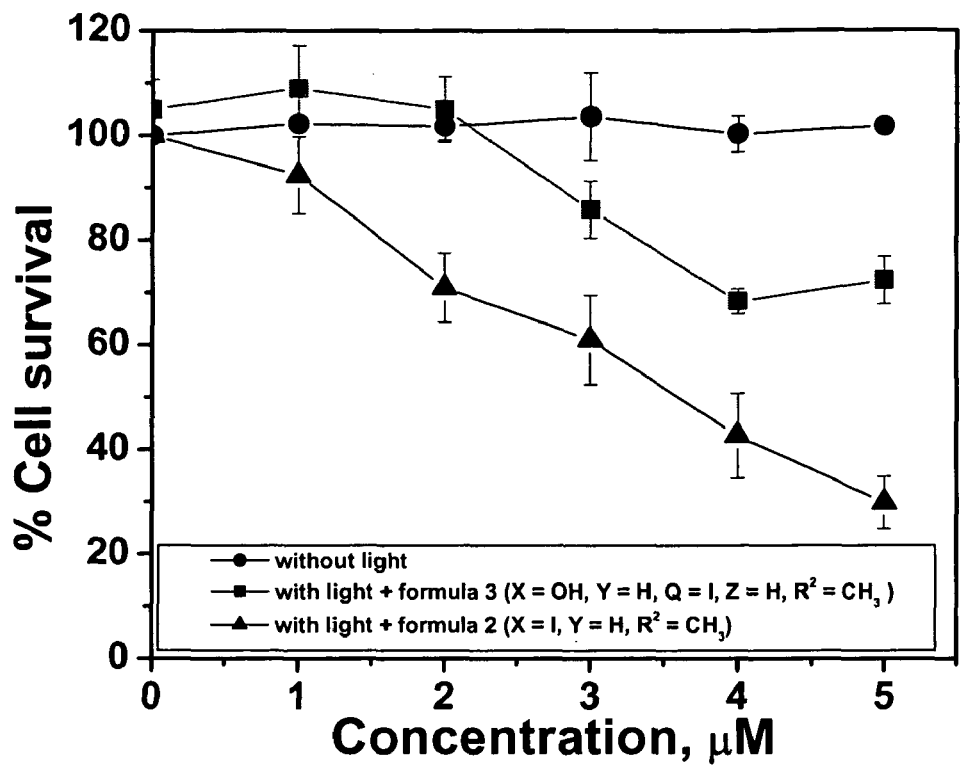

FIG. 5: Photocytotoxicity of the squaraine dyes of general formula 2, where X=I, Y=H, $R^2$=$CH_3$, and general formula 3, where X=OH, Y=H, Q=I, Z=H, $R^2$=$CH_3$ in L1210 mouse lymphoma cells. Data gives the number of cell (% of controls) counted after 48 h after the treatment for 22.5 min at 0° C. with various concentrations of the squaraine dyes under dark and under irradiation. Data points represent the mean of three independent experiments (±SD).

Figure 6:
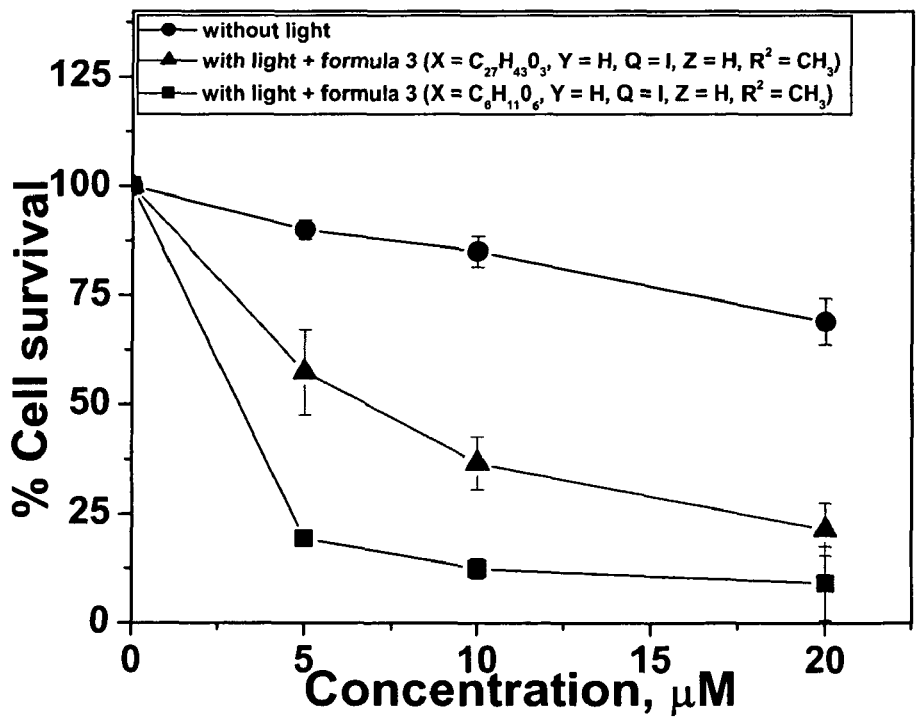

FIG. 6: Photocytotoxicity of the sugar linked and cholesterol-squaraine dyes of general formula 3, where X=$C_6H_{11}O_6$, Y=H, Q=I, Z=H, $R^2$=$CH_3$ and where X=$C_{27}H_{43}O_3$, Y=H, Q=I, Z=H, $R^2$=$CH_3$ L1210 mouse lymphoma cells. Data gives the number of cell (% of controls) counted after 48 h after the treatment for 22.5 min at 0° C. with various concentrations of the squaraine derivatives under dark and under irradiation. Data points represent the mean of three independent experiments (±SD).

Accordingly, the present invention relates to quinaldine based squaraine dyes of the general formulae 2 and 3 and semisquaraines of the general formula 1 and pharmaceutically acceptable derivatives thereof.

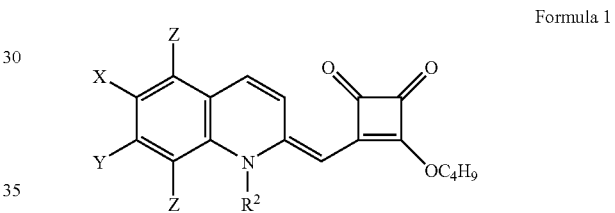

Formula 1 wherein, X=H, I, Br, $NO_2$, CN, COOH, $SO_3H$ or $OR^1$, wherein $R^1$=H, alkyl groups having from 1 to 6 carbon atoms, glycols having from 2 to 4 ethylene groups, cholic acid, cholesterol, sugar, amino acids or peptides, wherein Y=H, I, or Br, wherein, Z=H, I, Br, $NO_2$, CN, COOH, $SO_3H$, $SO_2Cl$ or $OR^1$, wherein $R^2$=alkyl groups having from 1 to 6 carbon atoms, glycols having from 2 to 4 ethylene groups, alkyl sulphonic acids and acid chlorides having from 1 to 6 carbon atoms

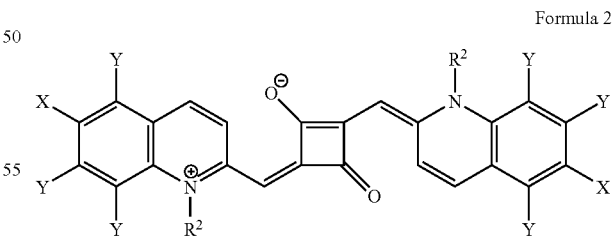

Formula 2 wherein, X=H, I, Br, $NO_2$, CN, COOH, $SO_3H$, $SO_2Cl$ or $OR^1$, wherein, $R^1$=H, alkyl groups having from 1 to 6 carbon atoms, glycols having from 2 to 4 ethylene groups, cholic acid, cholesterol, sugar, amino acids or peptides, wherein, Y=H, I, Br, $NO_2$, CN, COOH, $SO_3H$, $SO_2Cl$ or $OR^1$, wherein $R^2$=alkyl groups having from 1 to 6 carbon atoms, glycols having from 2 to 4 ethylene groups, alkyl sulphonic acids and acid chlorides having from 1 to 6 carbon atoms Formula 3

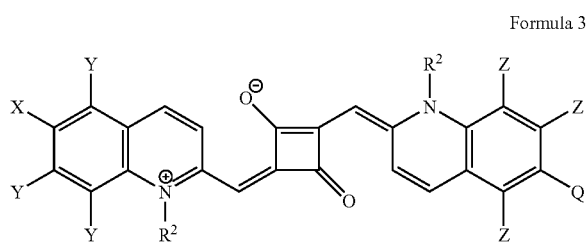

wherein, X=OR¹, wherein, R¹=H, alkyl groups having from 1 to 6 carbon atoms, glycols having from 2 to 4 ethylene groups, cholic acid, cholesterol, sugar, amino acids or peptides, wherein Y=H, I, Br, $NO_2$, CN, COOH, $SO_3H$, $SO_2Cl$ or OR¹, wherein Q=H, I, Br, $NO_2$, CN, COOH, $SO_3H$, $SO_2Cl$, wherein Z=H, I, Br, $NO_2$, CN, COOH, $SO_3H$, $SO_2Cl$, wherein R²=alkyl groups having from 1 to 6 carbon atoms, glycols having from 2 to 4 ethylene groups, alkyl sulphonic acids and acid chlorides having from 1 to 6 carbon atoms.

In one embodiment of the invention, the quinaldinium salt and squaric acid in the ratio 1:1 in a mixture of benzene and n-butanol (1:1) is refluxed at (90-110° C.) for a time period of 24-36 h. Removal of the solvent gave a residue, which was then subjected to column chromatography over silica gel to obtain compounds of the general formula 1.

In another embodiment of the of the invention, the quinaldinium salt and squaric acid in the ratio (2:1) in a solution of benzene and n-butanol (1:1) is refluxed for 24-36 h. Removal of the solvent gave a residue, which was then subjected to column chromatography over silica gel to obtain compounds of the general formula 2.

In another embodiment of the invention, the quinaldine based semisquaraines of the general formula 1 and the quinaldinium salts substituted with heavy atoms (halogen atoms) at the 6-position are heated in a mixture of benzene and n-butanol (1:1) at (90-110° C.) for a time period of 12-18 h. Removal of the solvent gave a residue, which was then subjected to column chromatography over silica gel to obtain compounds of the general formula 3.

In another embodiment of the invention, the compound of the formulae 1, 2 and 3 are used as photosensitizers in the photodynamic treatment of cancer and other related diseases.

In yet another embodiment of the invention, the compounds of the formulae 1, 2 and 3 are used as near infrared fluorescent sensors for the diagnosis of cancer.

The invention also relates to the use of compound of formulae 1, 2 and 3 as a sensitizer in the sterilization of fluids, water and related other applications.

In the present investigation, the quinaldine based semisquaraines of the general formula 1 have been synthesized. These semisquaraines were found to be unreactive towards quinaldinium salts containing electron-donating substituents. However, when refluxed with quinaldinium salts containing electron-withdrawing substituents like nitro, cyano and electro-negative substituents like halogen atoms, it is observed that the semisquaraines of the general formula 1 formed squaraine dyes of the general formula 3. Thus a highly efficient, two-step process for the synthesis of unsymmetrical squaraine dyes has been demonstrated.

In the present invention, novel quinaldine based squaraine dyes were synthesized and their photophysical and in vitro photobiological properties in the presence and absence of light were investigated. These dyes were found to have absorption in the near infrared region (700-750 nm). In the preparation of the compounds of the general formulae 2 and 3, the aromatic ring of the quinaldine moiety is modified with heavier halogen atoms such as bromine and iodine, this is to enable intersystem crossing efficiency of these dyes, which, in turn, would enhance the generation of highly reactive species like singlet oxygen.

In the present investigation, the aromatic ring of the quinaldine moiety is yet again modified with cholesterol and sugar moieties. Modification with cholesterol and sugar moieties is expected to increase the cell permeability and to bring about target specificity to these dyes since cholesterol is known to have membrane affinity and an accumulation of the esters in lipoprotein particles—and in consequence in proliferating cells and sugars are known to have affinity to the cancer cells.

In the present invention, we have investigated the cytotoxicity of these dyes in mammalian AS52 cells both in the presence and absence of light. It was found that the cytotoxicity of (sugar linked) squaraine dyes of general formula 3, where X=$C_6H_{11}O_6$, Y=H, Q=I, Z=H, R²=$CH_3$ and (cholesterol linked) where X=$C_{27}H_{43}O_3$, Y=H, Q=I, Z=H, R²=$CH_3$ are significantly high when compared with the (hydroxyl-substituted derivative) squaraine dye of general formula 3, where X=OH, Y=H, Q=I, Z=H, R²=$CH_3$. These dyes were found to be more cytotoxic than the diiodo squaraine dye of the general formula 2, where X=I, Y=H, R²=$CH_3$, which may be attributed to their increased cell permeability due to the presence of sugar and cholesterol moieties.

The following examples are given by way of illustration and therefore should not be construed to limit the scope of present investigation.

Examples 1-3 represent typical synthesis of compounds of the general formulae 1-3 and examples 4-7 represent the photophysical properties of general formulae 1-3 and examples 8 and 9 represent the in vitro cytotoxic properties of quinaldine based squaraine dyes of formulae 2 and 3.

EXAMPLE 1

General Procedure for the Preparation of Compounds Represented by Formula 1

A mixture of the corresponding quinaldinium salt (1 mmol), squaric acid (1 mmol) and quinoline (0.5 mL) was refluxed in a mixture of n-butanol and benzene (6-9 mL each, 1:1) with azeotropic distillation of water for 24-36 h. The solvent was distilled off under reduced pressure to obtain a residue which was chromatographed over silica gel. Elution of the column with a mixture (1:19) of methanol and chloroform gave the semisquaraines of the general formula 1.

The physiochemical properties of compound of the general formula 1, (wherein X=OH, Y=H and Z=H, R²=$CH_3$, 90-95%), mp 150-152° C., IR (KBr) $v_{max}$ 3412, 3042, 2963, 1761, 1606 $cm^{-1}$. ¹H-NMR ($CDCl_3$+DMSO-$d_6$, 1:4) δ 10.06 (1H, OH), 9.29 (1H, d, J=11.4 Hz), 7.89 (1H, d, J=9.3 Hz), 7.73 (1H, d, J=9.4 Hz), 7.34 (1H, d, J=9.3 Hz), 7.17 (1H, s), 6.14 (1H, s), 4.64 (2H, t, J=6.5 Hz), 4.11 (3H, s), 1.78 (2H, m), 1.45 (2H, m), 0.93 (3H, m). ¹³C NMR (DMSO-$d_6$, 1:4) δ 185.2, 177.2, 175.4, 171.5, 155.8, 152.5, 137.4, 132.8, 127.1, 124.5, 123.0, 119.4, 111.5, 95.6, 70.8, 37.8, 31.7, 18.2, 13.5; FAB-MS: m/z=325.140 (calcd 325.139 for $C_{19}H_{19}NO_4$).

The physiochemical properties of compound of formula 1, (wherein, X=OH, Y=Br, and Z=H, R²=$CH_3$, 80-90%), mp 182-184° C., IR (KBr) $v_{max}$ 3421, 2950, 1760, 1589 $cm^{-1}$. ¹H-NMR ($CDCl_3$+DMSO-$d_6$, 1:4) δ 9.31 (1H, d, J=9.2 Hz), 8.12 (1H, s), 7.88 (1H, d, J=9.2 Hz), 7.3 (1H, s), 6.15 (1H, s), 4.65 (2H, t, J=6.7 Hz), 4.09 (3H, s), 1.78 (2H, m), 1.48 (2H, m), 0.96 (3H, m). ¹³C NMR (DMSO-$d_6$, 1:4) δ 185.8, 177.3, 175.4, 172.0, 156.2, 136.2, 133.3, 126.1, 124.5, 123.2, 118.0, 111.4, 97.8, 71.8, 38.8, 31.5, 18.1, 13.3; FAB-MS: m/z=404.256 (calcd 404.255 for $C_{19}H_{18}BrNO_4$).

The physiochemical properties of compound of the general formula 1, (wherein, X=$OCH_2CH_3$, Y=H, and Z=H, $R^2$=$CH_3$, 80-90%), mp 184-186° C., IR (KBr) $\nu_{max}$ 3016, 2923, 1756, 1601 cm$^{-1}$. $^1$H-NMR (CDCl$_3$) δ 9.41 (1H, d, J=9.3 Hz), 7.84 (1H, d, J=9.3 Hz), 7.63 (1H, d, J=9.4 Hz), 7.33 (1H, d, J=9.5 Hz), 7.09 (1H, s), 6.15 (1H, s), 4.71 (2H, t, J=6.6 Hz), 4.14 (2H, t, J=6.9 Hz), 4.05 (3H, s), 1.78 (5H, m), 1.49 (2H, m), 0.96 (3H, m). $^{13}$C NMR (CDCl$_3$) δ 184.1, 176.3, 174.3, 170.2, 156.6, 153.3, 136.7, 126.6, 125.6, 122.8, 117.4, 109.5, 94.6, 71.9, 63.9, 37.1, 31.8, 18.2, 14.2, 13.5, 13.3; FAB-MS: m/z=353.164 (calcd 353.163 for $C_{21}H_{23}NO_4$).

The physiochemical properties of compound of the general formula 1, (wherein, X=$C_6H_{11}O_6$, Y=H, Z=H, $R^2$=$CH_3$, 85-90%), mp 162-164° C.); IR (KBr) $\nu_{max}$ 3029, 2943, 1762, 1591 cm$^{-1}$; $^1$H-NMR (DMSO-d$_6$) δ 9.19 (1H, d, J=9.4 Hz), 7.91 (1H, d, J=9.2 Hz), 7.73 (1H, d, J=9.4 Hz), 7.34 (1H, d, J=9.1 Hz), 7.17 (1H, s), 6.14 (1H, s), 6.01-5.62 (3H, m), 4.82-4.67 (2H, m), 3.98 (3H, s); $^{13}$C NMR (DMSO-d$_6$) δ 197.72, 190.81, 190.27, 165.65, 164.15, 164.12, 162.76, 138.63, 135.59, 129.19, 129.11, 128.96, 128.95, 128.42, 121.93, 118.49, 117.39, 115.66, 102.44, 96.78, 76.14, 73.33, 66.66, 62.22, 35.25, 31.75, 19.07, 13.77; FAB-MS: m/z=487.190 (calcd 487.184 for $C_{25}H_{29}NO_3$).

EXAMPLE 2

General Procedure for Preparation of Compounds Represented by the General Formula 2

A mixture of the corresponding quinaldinium salt (1 mmol), and squaric acid (0.5 mmol) and quinoline (0.5 mL) was refluxed in a mixture of n-butanol and benzene (6-9 mL each, 1:1) with azeotropic distillation of water for 24-36 h. The solvent was distilled off under reduced pressure to obtain a residue, which was chromatographed over silica gel. Elution of the column with a mixture (1:9) of methanol and chloroform gave the corresponding squaraine dyes of the general formula 2.

The physiochemical properties of compound of the general formula 2, (wherein, X=Br, Y=H, $R^2$=$CH_3$, 90-95%), mp 336-338° C., IR (KBr) $\nu_{max}$ 3056, 1613, 1580 cm$^{-1}$. $^1$H-NMR (DMSO-d$_6$) δ 9.31 (1H, d, J=9.5 Hz), 9.28 (1H, d, J=9.3 Hz), 7.3-8.4 (8H, m, aromatic), 5.86 (1H, s, vinylic), 5.78 (1H, s, vinylic), 3.85 (3H, s); 3.78 (3H, s); FAB-MS: m/z=550.246 (calcd 550.248 for $C_{26}H_{18}Br_2N_2O_2$).

The physiochemical properties of compound of the general formula 2, (wherein, X=I, Y=H, $R^2$=$CH_3$, 85-95%), mp 314-315° C., IR (KBr) $\nu_{max}$ 2962, 1620, 1553 cm$^{-1}$. $^1$H-NMR (DMSO-d$_6$) δ 9.23 (1H, d, J=9.4 Hz), 9.19 (1H, d, J=9.2 Hz), 7.1-8.05 (8H, m, aromatic), 5.89 (1H, s, vinylic), 5.72 (1H, s, vinylic), 3.81 (3H, s), 3.71 (3H, s); FAB-MS: m/z=643.944 (calcd 643.946 for $C_{26}H_{18}I_2N_2O_2$).

The physiochemical properties of compound of the general formula 2, (wherein X=CN, Y=H, $R^2$=$CH_3$, 80-90%), mp 290-292° C., IR (KBr) $\nu_{max}$ 3032, 1616, 1579 cm$^{-1}$. $^1$H-NMR (DMSO-d$_6$) δ 9.49 (1H, d, J=9.4 Hz), 9.45 (1H, d, J=9.5 Hz), 7.4-8.27 (8H, m, aromatic), 5.92 (1H, s, vinylic), 5.85 (1H, s, vinylic), 3.92 (3H, s), 3.84 (3H, s); FAB-MS: m/z=498.149 (calcd 498.150 for $C_{27}H_{22}N_4O_6$).

The physiochemical properties of compound of the general formula 2, (wherein X=$NO_2$, Y=H, $R^2$=$CH_3$, 75-82%), mp 306-308° C., IR $\nu_{max}$ (KBr) 3029, 2225, 1602 cm$^{-1}$; $^1$H-NMR (DMSO-d$_6$) δ 9.39 (1H, d, J=8.9 Hz), 9.42 (1H, d, J=9.4 Hz), 7.35-8.28 (8H, m, aromatic), 5.87 (1H, s, vinylic), 5.79 (1H, s, vinylic), 3.95 (3H, s), 3.82 (3H, s); FAB-MS: m/z=442.472 (calcd 442.470 for $C_{28}H_{18}Br_2N_4O_2$).

The physiochemical properties of compound of the general formula 2, (wherein X=$C_{27}H_{43}O_3$, (cholesterol), Y=H, $R^2$=$CH_3$, 75-85%), mp 328-330° C., $^1$H-NMR (CDCl$_3$) δ 9.31 (1H, d, J=9.57 Hz), 7.44-7.30 (4H, m, aromatic), 5.80 (1H, s, vinylic), 5.43 (1H, s), 4.60 (1H, s), 3.79 (3H, s), 2.50 (3H, s); 2.04-0.69 (46H, m); FAB-MS: m/z=1204.821 (calcd 1204.815 for $C_{80}H_{104}N_2O_7$).

The physiochemical properties of the compound of the general formula 2, (wherein X=$C_{41}H_{32}O_{11}$ (β-D-glucose with the hydroxyl groups protected with Benzoyl chloride), Y=H, $R^2$=$CH_3$, 75-80%), mp 294-296° C., $^1$H-NMR (CDCl$_3$) δ 9.17 (1H, d, J=9.32 Hz), 7.98-7.86 (23H, m, aromatic), 7.53-7.02 (47H, m, aromatic), 7.44-7.30 (4H, m, aromatic), 6.01 (3H, m), 5.79-5.73 (7H, m), 5.46 (1H, s), 4.67-4.59 (5H, m), 4.17 (2H. s), 3.62 (6H, s); FAB-MS: m/z=1564.469 (calcd 1564.478 for $C_{94}H_{72}N_2O_{21}$).

EXAMPLE 3

General Procedure for Preparation of Compounds Represented by the General Formula 3

A mixture of the corresponding semisquaraine (1 mmol) and the iodo or bromo substituted quinaldinium salt (1 mmol), and quinoline (0.5 mL) were refluxed in a mixture of n-butanol and benzene (6-9 mL each, 1:1) with azeotropic distillation of water for 18-24 h. The solvent was distilled off under reduced pressure to obtain a residue, which was chromatographed over silica gel. Elution of the column with a mixture (1:9) of methanol and chloroform gave the corresponding squaraine dye.

The physiochemical properties of compound of the general formula 3, (wherein X=OH, Q=I, Y=H, Z=H, $R^2$=$CH_3$, 90%), 325° C., IR (KBr) $\nu_{max}$ 3442, 3046, 1729, 1621, 1579, 1560 cm$^{-1}$. $^1$H-NMR (DMSO-d$_6$) δ 10.2 (1H, OH), 9.29 (1H, d, J=9.2 Hz), 9.01 (1H, d, J=9.5 Hz), 7.86-7.01 (8H, m), 5.77 (1H, s, vinylic), 5.44 (1H, s, vinylic), 3.9 (3H, s), 3.5 (3H, s); FAB-MS: m/z=534.040 (calcd 534.039 for $C_{26}H_{19}IN_2O_3$).

The physiochemical properties of compound of the general formula 3, (wherein X=$C_6H_{11}O_6$ (β-D-glucose), Q=I, Y=H, Z=H, $R^2$=$CH_3$, 85-92%), mp 316-318° C., $^1$H-NMR (DMSO-d$_6$) δ 9.32 (1H, d, J=9.2 Hz), 9.13 (1H, d, J=9.5 Hz), 8.10-7.21 (8H, m), 6.12-6.01 (3H, m), 5.82-5.68 (4H, m), 3.86 (3H, s), 3.76 (3H, s); FAB-MS: m/z=696.091 (calcd 696.097 for $C_{32}H_{29}IN_2O_8$).

The physiochemical properties of compound of the general formula 3, (wherein, X=$C_{41}H_{32}O_{11}$ (β-D-glucose with the hydroxyl groups protected with benzoyl chloride), Y=H, Z=H, Q=I, $R^2$=$CH_3$, 85-95%), mp 302-304° C., $^1$H-NMR (CDCl$_3$) δ 9.11 (1H, d, J=8.6 Hz), 7.98-7.86 (12H, m), 7.53-7.02 (13H, m), 6.01 (3H, m), 5.79-5.46 (4H, m), 5.46 (1H, d, 7.2 Hz), 3.9 (3H, s), 3.6 (3H, s); FAB-MS: m/z=1112.210 (calcd 1112.202 for $C_{60}H_{45}IN_2O_{12}$).

The physiochemical properties of compound of the general formula 3, (wherein X=$C_{27}H_{43}O_3$, cholesterol, Y=H, Q=I, Z=H, $R^2$=$CH_3$, 86-90%), mp 328-330° C., $^1$H-NMR (CDCl$_3$) δ 9.16 (1H, d, J=9.3 Hz), 9.08 (1H, d, J=9.1 Hz), 8.46-7.81 (8H, m, aromatic), 5.93 (1H, s, vinylic), 5.84 (1H, s, vinylic), 5.4 (1H, s), 4.6 (1H, m), 3.94 (3H, s); 3.81 (3H, s), 2.04-0.69 (48H, m) FAB-MS: m/z=933.389 (calcd 933.382 for $C_{53}H_{61}IN_2O_5$).

EXAMPLE 4

Semisquaraine of the general formula 1 in which a quinaldine moiety is linked to the squaric acid through methylene bridge have absorption around 480 nm with high molar extinction coefficient ($4.0 \times 10^4$ M$^{-1}$ cm$^{-1}$) which depends on the substitution on the quanaldine unit. For example semisquaraines with —OH groups at the $6^{th}$ position showed absorption maxima at 477 nm while semisquaraines with —OEt group at $6^{th}$ position showed absorption maxima at 478 nm in methanol. They showed good fluorescence emission with emission maximum ranging from 550-600 nm. The absorption and fluorescence emission spectra of representative semisquaraine of the general formula 1 where X=OH, Y=H, Z=H, $R^2$=CH$_3$ are shown in FIG. 1.

EXAMPLE 5

Figure 2:
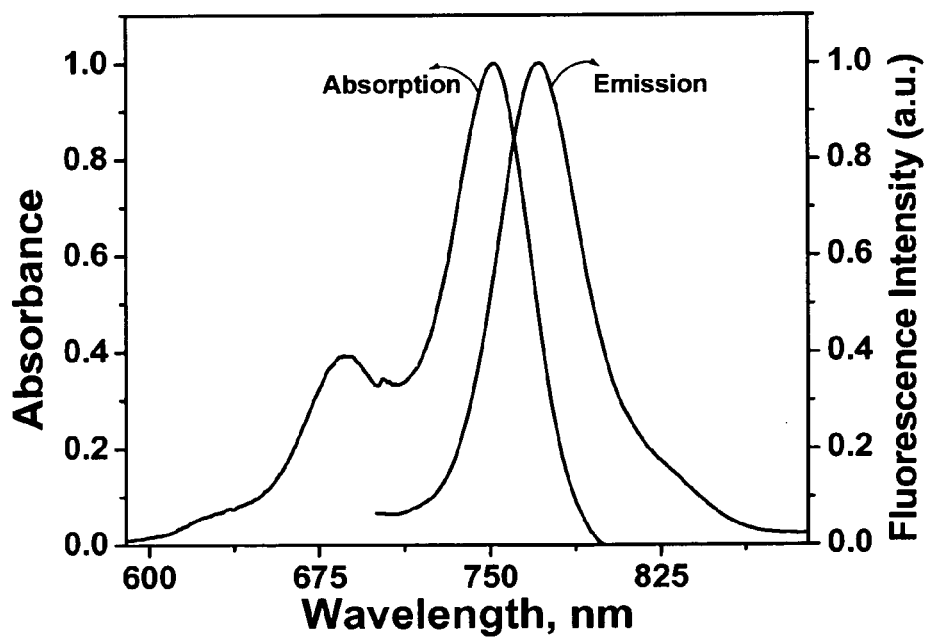

Squaraine dyes of the general formula 2 showed good absorption in the long wavelength region. Similar to the semisquaraines the absorption spectra of these dyes were also dependent on the substitution on the quinaldine moiety. For example, dye of the general formula 2, where X=I, Y=H, $R^2$=CH$_3$, showed absorption maxima at around 750 nm in DMSO, whereas dyes of the general formula 2, wherein X=CN, Y=H, $R^2$=CH$_3$ and X=NO$_2$, Y=H, $R^2$=CH$_3$ showed absorption maxima around 615 nm and 618 nm respectively, in methanol. The presence of electron withdrawing groups in the quinaldine ring shifts the absorption maxima towards the blue region. Similarly the emission spectra of these dyes showed a shift in the emission maxima depending on the substituents present. For example, dye of the general formula 2, where X=I, Y=H, $R^2$=CH$_3$, showed emission maxima at around 772 nm in dimethyl sulfoxide, whereas dye of the general formula 2, wherein X=CN, Y=H, $R^2$=CH$_3$ showed emission maxima around 647 nm, in methanol. The absorption and fluorescence emission spectra of representative symmetrical squaraine dye of the general formula 2, where X=I, Y=H, $R^2$=CH$_3$ are shown in FIG. 2.

EXAMPLE 6

Demonstration of Formation of Unsymmetrical Squaraine Dyes of the General Formula 3

FIG. 3 shows the absorption spectra recorded at various time intervals for the reaction between semisquaraines of the general formula 1, where X=OH, Y=H, Z=H, $R^2$=CH$_3$, and halogenated (Iodo or Bromo) quinaldinium salts. As seen from the figure, initially only the absorption from the semisquaraine is observed at 485 nm. As the reaction progresses a new band at 715 nm appears and intensifies with time showing the formation of the dye. Interestingly, it was observed that the semisquaraines of the general formula 1 reacted only with quinaldinium salts having electron withdrawing substituents like nitro, cyano and electronegative groups like iodo and bromo. Reaction of the semisquaraines with quinaldinium salts having electron donating substituents like OH, OEt did not yield any products (Inset of FIG. 3). Thus the specificity of the semisquaraines towards quinaldinium salts with electron withdrawing substituents is demonstrated, which enables the synthesis of a library of unsymmetrical squaraine dyes that can be used for photodynamic and therapeutical application.

EXAMPLE 7

Similar to the symmetrical dyes, unsymmetrical squaraine dyes of the general formula 3 showed good absorption in the long wavelength region. For example dye of the general formulae 3, wherein X=C$_6$H$_{11}$O$_6$, Y=H, Q=I, Z=H, $R^2$=CH$_3$, and X=OH, Y=H, Q=I, Z=H, $R^2$=CH$_3$ showed absorption maxima in the range 745-755 nm and emission maxima in the range 765-775 nm in DMSO. The absorption and fluorescence emission spectra of representative unsymmetrical squaraine dyes of the general formula 3, where X=C$_6$H$_{11}$O$_6$, Y=H, Q=I, Z=H, $R^2$=CH$_3$, are shown in FIG. 4.

EXAMPLE 8

Cytotoxicity Induced by Squaraine Dyes of the General Formulae 2 and 3

In order to analyze the cytotoxicity of the squaraine dyes of the general formula 2 wherein X=I, Y=H, $R^2$=CH$_3$ and 3 wherein X=OH, Y=H, Q=I, Z=H, $R^2$=CH$_3$, with and without visible light, the cloning efficiencies of L1210 mouse lymphoma cells exposed to various concentrations of the dyes were determined. The light exposure was carried out from a 1000 W halogen lamp at a distance of 33 cm in Ca$^{2+}$ and Mg$^{2+}$ free PBS (140 mM NaCl, 3 mM KCl, 8 mM Na$_2$PH$_4$, pH 7.4) on ice (10$^6$ cells/mL). Illumination for 10 min corresponds to 225 kJ/m$^2$ between 400 and 800 nm. The cells were pelleted by centrifugation and resuspended in PBSG three times. The cells were resuspended at $3 \times 10^4$ cells/mL in fresh medium at 37° C. and the numbers of cells were counted repeatedly for 60 h. From the exponential part of the growth curves (between 24 and 60 h) the number of proliferating cells at the time of resuspension was calculated by extrapolation. Cell survival was defined as the ratio between proliferating and resuspended cells. Results obtained with representative quinaldine based squaraine dyes of the general formula 2 wherein X=I, Y=H, $R^2$=CH$_3$ and 3 wherein X=OH, Y=H, Q=I, Z=H, are shown in FIG. 5.

From the results it is clear that the squaraine dyes of the general formula 2 wherein X=I, Y=H, $R^2$=CH$_3$ and 3 wherein X=OH, Y=H, Q=I, Z=H, $R^2$=CH$_3$, show a dose dependent photocytotoxicity. i.e. the % of cell survival decreases with the increasing concentration of dyes of the formula the general formula 2 and 3 under illumination conditions indicating their high cell killing efficiency under these conditions. At the same time these dyes are found to be less toxic in the dark indicating their non-toxicity in the absence of light. These results clearly demonstrate the photodynamic therapeutical applications of quinaldine based squaraine dyes. Of the two, dye of the general formula 2, wherein X=I, Y=H, $R^2$=CH$_3$ is found to be more toxic than the dye of the general formula 3, wherein X=OH, Y=H, Q=I, Z=H, $R^2$=CH$_3$.

EXAMPLE 9

Cytotoxicity Induced by Squaraine Dyes of the General Formulae 3 where the Dyes are Conjugated with Cellular Recognition Elements The cytotoxicity induced by squaraine dyes of the general formula 3 wherein X=C$_6$H$_{11}$O$_6$, Y=H, Q=I, Z=H, $R^2$=CH$_3$ and X=C$_{27}$H$_{43}$O$_3$, Y=H, Q=I, Z=H, $R^2$=CH$_3$ in mouse lymphoma cells L1210 with and without visible light, was carried out as explained in EXAMPLE 8. Results obtained with representative quinaldine based squaraine dyes of the general formula 3 wherein X=C$_6$H$_{11}$O$_6$, Y=H, Q=I, Z=H, $R^2$=CH$_3$ and X=C$_{27}$H$_{43}$O$_3$, Y=H, Q=I, Z=H, $R^2$=CH$_3$ are shown in FIG. 6.

It is clear from FIG. 6 that the squaraine dyes of the general formula 3 wherein X=C$_6$H$_{11}$O$_6$, Y=H, Q=I, Z=H, $R^2$=CH$_3$ and X=C$_{27}$H$_{43}$O$_3$, Y=H, Q=I, Z=H, $R^2$=CH$_3$ show a dose dependent photocytotoxicity. i.e. the % of cell survival decreases with the increasing concentration of dyes under illumination conditions indicating their high cell killing efficiency under these conditions. These dyes show very less toxicity in the absence of light thereby demonstrating their photodynamic therapeutical application. The dye of the general formula 3 wherein $X=C_6H_{11}O_6$, $Y=H$, $Q=I$, $Z=H$, $R^2=CH_3$ showed higher toxicity than the dye of the general formula 3 wherein $X=C_{27}H_{43}O_3$, $Y=H$, $Q=I$, $Z=H$, $R^2=CH_3$.

The quinaldine based squaraine dyes of the present invention possess satisfactory properties of a photosensitizer for photodynamic therapeutical and industrial applications.

The Main Advantages of these Systems Include:

1. Semisquaraines, symmetrical and unsymmetrical squaraine dyes represented by formulae 1, 2 and 3 are novel and pure single substances.
2. Their synthetic methodology is very economical
3. Symmetrical and unsymmetrical squaraine dyes represented by formulae 2 and 3 possess absorption in the near-infrared region (700-750 nm)
4. They are nontoxic in the dark but show good cell killing properties when exposed to light, as expected of an ideal photosensitizer
5. Their benzo ring can be substituted with various functional groups so as to have increased cellular uptake and localisation.
6. They can be conjugated with cellular recognition elements like cholesterol and sugar so as to bring about site specific tumor localisation and destruction.
7. They can be used for photodynamic industrial applications such as sterilization of water etc.
8. They can be used as near-infrared fluorescence sensors in biological applications.
9. They can be used for the detection of biologically important metal ions under physiological conditions.

We claim:

1. A semisquaraine of Formula 1

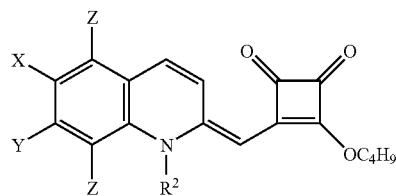

Formula 1 wherein
$X=H$, I, Br, $NO_2$, CN, COOH, $SO_3H$ or $OR^1$,
   wherein $R^1=H$, alkyl group having from 1 to 6 carbon atoms, glycol having from 2 to 4 ethylene group, cholic acid, cholesterol, sugar, amino acid or peptide,
$Y=H$, I, or Br,
$Z=H$, I, Br, $NO_2$, CN, COOH, $SO_3H$, $SO_2Cl$ or $OR^1$ and
$R^2$=alkyl group having from 1 to 6 carbon atoms, glycol having from 2 to 4 ethylene group, alkyl sulphonic acid or acid chloride having from 1 to 6 carbon atoms
with a proviso that when $R^2=CH_3$, Z is not H.

2. A process for the preparation of a semisquaraine of the Formula 1

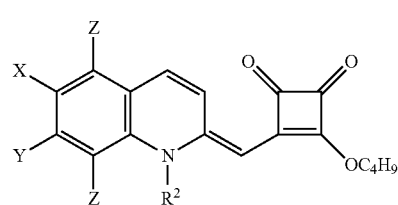

Formula 1 wherein
$X=H$, I, Br, $NO_2$, CN, COOH, $SO_3H$ or $OR^1$,
   wherein $R^1=H$, alkyl group having from 1 to 6 carbon atoms, glycol having from 2 to 4 ethylene group, cholic acid, cholesterol, sugar, amino acid or peptide,
$Y=H$, I, or Br,
$Z=H$, I, Br, $NO_2$, CN, COOH, $SO_3H$, $SO_2Cl$ or $OR^1$, and
$R^2$=alkyl group having from 1 to 6 carbon atoms, glycol having from 2 to 4 ethylene group, alkyl sulphonic acid or acid chloride having from 1 to 6 carbon atoms,
with a proviso that when $R^2=CH_3$, Z is not H
said process comprising
reacting quinaldinium salt and squaric acid in a mixture of benzene and n-butanol under stirring,
removing the solvent and
purifying the residue obtained to obtain compound of Formula 1.

3. A process as claimed in claim 2 wherein the quinaldinium salt and squaric acid are present in a ratio of 1:1.

4. A process as claimed in claim 2 wherein the ratio of benzene to n-butanol is 1:1.

5. A process as claimed in claim 2 wherein the stirring is carried out at a temperature in the range of 90° C.-110° C. and for a time period of 24 hours-36 hours.

6. A process as claimed in claim 2 wherein the solvent is removed by evaporation.

7. A process as claimed in claim 2 wherein the purification is effected by column chromatography over silica gel.

8. Quinaldine based symmetrical squaraine dye of Formula 2 below or pharmaceutically acceptable salts thereof

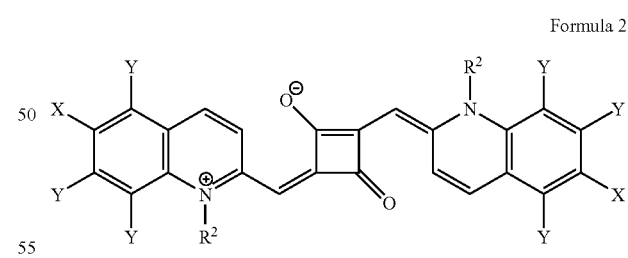

Formula 2 wherein
$X=H$, I, Br, $NO_2$, CN, COOH, $SO_3H$, $SO_2Cl$ or $OR^1$,
   wherein, $R^1=H$, alkyl group having from 1 to 6 carbon atoms, glycol having from 2 to 4 ethylene group, cholic acid, cholesterol, sugar, amino acid or peptide,
$Y=H$, I, Br, $NO_2$, CN, COOH, $SO_3H$, $SO_2Cl$ or $OR^1$,
$R^2$=alkyl group having from 1 to 6 carbon atoms, glycol having from 2 to 4 ethylene group, alkyl sulphonic acid or acid chloride having from 1 to 6 carbon atoms,
with a proviso that when $X=H$ and $R^2=CH_3$ or $C_2H_5$, Y is not H.

9. Process for the preparation of a quinalidine based symmetrical squaraine dye of Formula 2

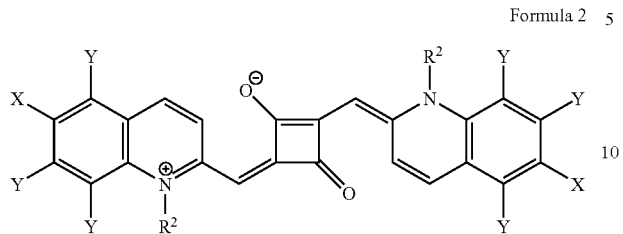

Formula 2 wherein
X=H, I, Br, $NO_2$, CN, COOH, $SO_3H$, $SO_2Cl$ or $OR^1$,
  wherein, $R^1$=H, alkyl group having from 1 to 6 carbon atoms, glycol having from 2 to 4 ethylene group, cholic acid, cholesterol, sugar, amino acid or peptide,
Y=H, I, Br, $NO_2$, CN, COOH, $SO_3H$, $SO_2Cl$ or $OR^1$,
$R^2$=alkyl group having from 1 to 6 carbon atoms, glycol having from 2 to 4 ethylene group, alkyl sulphonic acid or acid chloride having from 1 to 6 carbon atoms,
with a proviso that when X=H and $R^2$=$CH_3$ or $C_2H_5$, Y is not H
said process comprising:
reacting a quinaldinium salt and squaric acid in a solution of benzene and n-butanol with stirring,
removing said solvent and
purifying the residue so obtained to obtain the squaraine dye of Formula 2.

10. A process as claimed in claim 9 wherein the quinaldinium salt and squaric acid are present in a ratio of 2:1.

11. A process as claimed in claim 9 wherein the ratio of benzene to n-butanol is 1:1.

12. A process as claimed in claim 9 wherein the stirring is carried out at a temperature in the range of 90° C.-110° C. and for a time period of 24 hours-36 hours.

13. A process as claimed in claim 9 wherein the solvent is removed by evaporation.

14. A process as claimed in claim 9 wherein the purification is effected by column chromatography over silica gel.

15. A quinaldine based asymmetrical squaraine dye of Formula 3

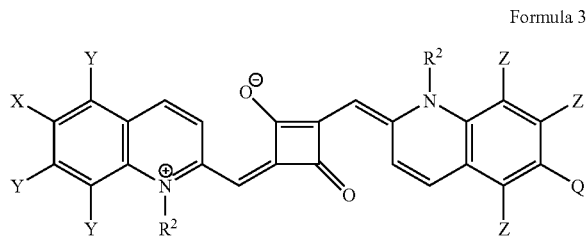

Formula 3 wherein
X=$OR^1$,
  wherein $R^1$=H, alkyl group having from 1 to 6 carbon atoms, glycol having from 2 to 4 ethylene group, cholic acid, cholesterol, sugar, amino acid or peptide,
Y=H, I, Br, $NO_2$, CN, COOH, $SO_3H$, $SO_2Cl$ or $OR^1$,
Q=H, I, Br, $NO_2$, CN, COOH, $SO_3H$, $SO_2Cl$,
Z=H, I, Br, $NO_2$, CN, COOH, $SO_3H$, $SO_2Cl$, and
$R^2$=alkyl group having from 1 to 6 carbon atoms, glycol having from 2 to 4 ethylene group, alkyl sulphonic acid and acid chloride having from 1 to 6 carbon atoms,
with a proviso that when X=OH, $R^2$=$CH_3$, Y=H, and Z=H, Q is not I.

16. A process for the preparation of a quinaldine based asymmetrical squaraine dye of Formula 3

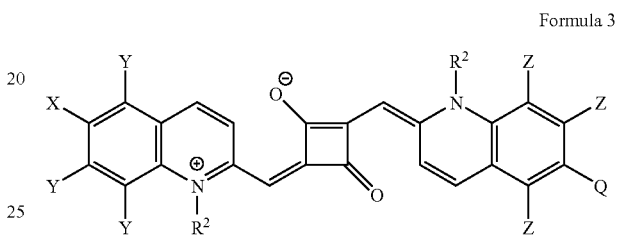

Formula 3 wherein
X=$OR^1$,
  wherein $R^1$=H, alkyl group having from 1 to 6 carbon atoms, glycol having from 2 to 4 ethylene group, cholic acid, cholesterol, sugar, amino acid or peptide,
Y=H, I, Br, $NO_2$, CN, COOH, $SO_3H$, $SO_2Cl$ or $OR^1$,
Q=H, I, Br, $NO_2$, CN, COOH, $SO_3H$, $SO_2Cl$,
Z=H, I, Br, $NO_2$, CN, COOH, $SO_3H$, $SO_2Cl$, and
$R^2$=alkyl group having from 1 to 6 carbon atoms, glycol having from 2 to 4 ethylene group, alkyl sulphonic acid and acid chloride having from 1 to 6 carbon atoms,
with a proviso that when X=OH, $R^2$=$CH_3$, Y=H, and Z=H, Q is not I
said process comprising
heating a quinaldine based semisquaraine of Formula 1 and quinaldinium salts substituted with halogen atoms at 6-position in a mixture of benzene and n-butanol,
removing the solvent to obtain a residue which on purification provides compound of Formula 3.

17. A process as claimed in claim 16 wherein the ratio of benzene to n-butanol is 1:1.

18. A process as claimed in claim 16 wherein the heating is carried out to a temperature in the range of 90° C.-110° C. and for a time period of 12 hours-18 hours.

19. A process as claimed in claim 16 wherein the solvent is removed by evaporation.

20. A process as claimed in claim 16 wherein the purification is effected by column chromatography over silica gel.

* * * * *